United States Patent [19]
Muroki

[11] Patent Number: 5,944,685
[45] Date of Patent: Aug. 31, 1999

[54] SKIN-CONTACT TYPE MEDICAL TREATMENT APPARATUS

[75] Inventor: Masahisa Muroki, Kanazawa, Japan

[73] Assignee: Polytronics, Ltd., Kanazawa-shi, Japan

[21] Appl. No.: 08/824,653

[22] Filed: Mar. 24, 1997

Related U.S. Application Data

[63] Continuation-in-part of application No. 08/797,482, Feb. 6, 1997, Pat. No. 5,848,985.

[30] Foreign Application Priority Data

Feb. 9, 1996 [JP] Japan ........................................ 8-24245
Nov. 21, 1996 [JP] Japan ..................................... 8-310848

[51] Int. Cl.$^6$ ..................................................... A61N 1/30
[52] U.S. Cl. ............................................. 604/20; 607/149
[58] Field of Search .......................... 604/20–21; 607/1, 607/72, 2, 3, 152, 149; 429/3

[56] References Cited

U.S. PATENT DOCUMENTS

| | | |
|---|---|---|
| 4,619,252 | 10/1986 | Ibbott . |
| 4,767,401 | 8/1988 | Seiderman . |
| 4,976,705 | 12/1990 | Aki et al. . |
| 4,976,706 | 12/1990 | Aki et al. . |
| 5,002,527 | 3/1991 | Reller et al. . |
| 5,053,001 | 10/1991 | Reller et al. . |
| 5,637,084 | 6/1997 | Kontturi et al. . |
| 5,685,837 | 11/1997 | Horstmann . |
| 5,772,688 | 6/1998 | Muroki . |

*Primary Examiner*—Mark Bockelman
*Attorney, Agent, or Firm*—Frishauf, Holtz, Goodman, Langer & Chick, P.C.

[57] ABSTRACT

A first conductive sheet film is disposed on a partial area of the skin-contact surface of an adhesive member. A conductive matrix is disposed on the first conductive film, the conductive matrix being dispersed with a drug to be permeated through skin. A second conductive film is disposed on the conductive matrix, the second conductive film having a plurality of openings distributed on the surface of the conductive matrix and having a standard single electrode potential lower than that of the first conductive film. An insulating film is disposed between the conductive matrix and the second conductive film in a manner such that an electric short path is not formed between the conductive matrix and the second conductive film. The insulating film has a plurality of openings distributed on the surface of the conductive matrix, and a connection member electrically interconnects the first and second conductive films.

6 Claims, 9 Drawing Sheets

SKIN-CONTACT TYPE MEDICAL TREATMENT APPARATUS

CROSS REFERENCE TO RELATED APPLICATIONS

This application is a continuation-in-part application of U.S. patent application Ser. No. 08/797,482 filed on Feb. 6, 1997, now U.S. Pat. No. 5,848,985, the entire contents of which are incorporated herein by reference.

This application is based on Japanese application Nos. Hei 8-310848 filed in Japan on Nov. 21, 1996, Hei 8-024245 filed in Japan on Feb. 9, 1996, and Hei 6-220193 filed in Japan on Sep. 14, 1996, the entire contents of all of which are incorporated herein by reference.

BACKGROUND OF THE INVENTION a) Field of the Invention

The present invention relates to a transcutaneous dosing element using iontophoresis.

b) Description of the Related Art

Transcutaneous dosing is an excellent drug delivery system for dosing a particular area of a living body with a drug at a predetermined density. Transcutaneous dosed drugs circulate with blood in a living body at a smaller percentage than venously injected or orally dosed drugs so that harmful side effects may be reduced and the amount of drug can be reduced. For these reasons, transcutaneous dosing can be utilized not only to alleviate inflammation and pain, but also to remedy some chronic diseases while patients may be able to continue normal daily living depending on the degree of seriousness of the diseases. For example, transcutaneous dosing may be applied for treatment of chronic diseases of muscular and osteal systems, for prevention of heart attack, for alleviation of bronchitis, and for treatment of nervous system disease.

For general transcutaneous dosing, a plaster coated with a matrix (meaning not a lattice shape of circuit devices, but base material containing effective drug components) is put in contact with a particular skin area to permeate a drug through subcutaneous tissues at a predetermined density, by means of concentration diffusion. Transcutaneous drugs effective for medical treatment are generally made of high polymer compounds and have a complicated three-dimensional structure. Therefore, use of simple concentration diffusion phenomenon may often result in insufficient treatment effects because drugs with a necessary concentration do not reach an affected part. The skin of a human body has a complicated multi-layer structure and a function of preventing foreign particles from being externally permeated. It is therefore not easy for high polymer drugs to permeate through subcutaneous tissues by overcoming the skin barrier.

As techniques for improving an effective permeation of transcutaneous dosing, use of iontophoresis and recently use of a polymer drug mixed with an absorption accelerator have drawn attention.

With the former techniques, effective components of a drug are ionized. An external electric power is applied between two electrodes (active and counter electrodes) mounted on skin to form an electric path via the skin, with one of the electrodes the, active electrode, being coated with effective components of the ionic drug, so that these components are forcibly migrated through the electric path in the skin by electric repulsion force. With the latter techniques, and, substance such as limonene, which can weaken the molecular bonding force of sebum and make the drug easy to permeate through the stratum corneum, is mixed with the drug in the matrix.

Although some of these techniques are practically used, they are still in the midst of development. Namely, the former techniques is associated with a problem of an external power source, and the latter techniques is associated with medical inefficacy.

As an external power source of iontophoresis, a fixed d.c. power source of about 100 V is used under the supervision of doctors in a hospital or the like, because the skin electric path is highly resistant (10 to 100 MΩ/cm). However, since patients cannot continue normal daily living with the fixed power source, a portable compact power source (battery) is generally used. After the battery is used for some period of time, its electromotive force lowers suddenly. The effects of drug permeation by cataphoresis may lower correspondingly, or if the skin resistance lowers greatly because of a change in the conditions of skin-contact surface or perspiration, large current will flow and the skin surface may be damaged.

As a means for solving such problems, another iontophoreses has been proposed (Japanese Patent Laid-open Publication No. 60-203270) in which two metals having different ionization tendencies are ohmically-contacted at an outer side of skin to generate an electromotive force by using an electrically closed circuit formed when the metals are put in contact with skin, and ionic drug made of metallic salt of the same type as a metal forming the positive pole of a cell is coated on the skin-contact surface of an electrode forming the positive pole of the cell. As opposed to the conventional technique using an external power source (battery), this approach uses the internal reaction of a cell (oxidation-reduction reaction between electrodes). This method is also associated, however, with the following problem. When an electrically closed circuit is formed via skin, electrons start to flow from the electrode forming the negative pole of the cell (negative electrode) having a larger ionization tendency toward the electrode forming the positive pole (positive electrode), and the negative electrode from which electrons moved outside (oxidized) becomes chemically active. Since the negative electrode is surrounded with water molecules, it is obvious that before negative ions are pulled from the living skin, the following reaction occurs:

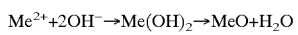

where $Me^{2+}$ is ion of the metal constituting the negative electrode. The cell electromotive force therefore changes greatly. For example, if a magnesium alloy is used for the negative electrode, which is recommended in Japanese Patent Laid-open Publication No. 60-203270, the surface of the negative electrode is coated with MgO in a short time. Since $Mg(OH)_2$ and MgO are insulating materials, the electromotive force lowers quickly and iontophoresis stops eventually.

In order to solve this problem, the present inventor has proposed a skin-contact power generation type iontophoresis power source using a combination of a semiconductor electrode forming the negative pole of a cell and a metal electrode forming the positive pole of the cell (Japanese Patent Laid-open Publication No. Hei 3-16573), which is herein incorporated by reference. This power source as well as an ionic drug coated on the positive electrode are put in contact with skin to form an electrically closed circuit. As electrons start to flow from the semiconductor negative electrode to the metal positive electrode, holes generated at the semiconductor negative electrode drift toward the skin-contact surface, while being self-biased by an internal electric field of the Schottky barrier formed at the skin-contact surface, and permeate through the skin in the form of free holes or semiconductor ions. Therefore, the semiconductor negative electrode maintains electrical neutrality and becomes durable and stable for long term use.

This power source automatically stops generation of electric power when the electrodes are short-circuited on the skin-contact surface by perspiration or the like. Skin can therefore be protected safely, inlike as in the case of external power source.

For transcutaneous dosing by iontophoresis, it is preferable if a transcutaneous dosing element has a size and shape suitable for an affected part. It is also preferable if a transcutaneous dosing element is disposable so as to allow a patient to receive continuous dosing while continuing normal daily living.

The skin-contact power generation type iontophoresis element using the semiconductor negative electrode is, however, difficult for a patient to change the shape thereof or cut into small area elements, because the conductive matrix with the ionic drug is disposed under the metal positive electrode which is electrically connected via a wire to the semiconductor negative electrode at the remote position.

If a high polymer drug is permeated through skin by iontophoresis, a permeation density often becomes insufficient even if a power source voltage is raised or current is increased. In such a case, it is effective to physiologically activate skin cells and raise the dosing efficacy.

SUMMARY OF THE INVENTION

It is an object of the present invention to provide a transcutaneous dosing element of a disposable skin-contact power generation type which is cost effective and relatively easy to use as a small area element and whose shape is easy to change.

It is another object of the present invention to provide a transcutaneous dosing element capable of artificially activating the physiological nature of skin.

According to one aspect of the present invention, there is provided a transcutaneous dosing element comprising: an adhesive sheet member having a skin-contact surface; a first conductive sheet film disposed on a partial area of the skin-contact surface of the adhesive member; conductive matrix disposed on the first conductive film, the conductive matrix being dispersed with ionic substance to be permeated through skin; a second conductive film disposed on the conductive matrix, the second conductive film having a plurality of openings distributed on the surface of the conductive matrix; an insulating film disposed between the conductive matrix and the second conductive film not to form an electric contact between the conductive matrix and the second conductive film, the insulating film having a plurality of openings distributed on the surface of the conductive matrix; a connection member for electrically interconnecting the first conductive film and the second conductive film; and electromotive force generating means for generating an electromotive force at an electric circuit comprising the first conductive film, the conductive matrix, skin, the second conductive film, and the connection member, when the adhesive member is adhered to skin.

The transcutaneous dosing element has a laminated structure of the second conductive film, the insulating film, the conductive matrix, the first conductive film, and the adhesive member. A patient who buys a transcutaneous dosing element of a predetermined size can cut it down to a proper size and shape to use it by electrically shorting the first and second conductive films at the peripheral area of the cut sheet.

As the conductive matrix (conductive gel substance dispersed with ionic substance) and the second conductive film are simultaneously put in contact with skin by using the adhesive member, a chemical cell is formed at the skin-contact area which cell is an external short-circuit type including the first conductive film (positive pole), the second conductive film (negative pole), the conductive matrix, and skin (electrolyte). The current path is a closed circuit constituted of the second conductive film→connection member→first conductive film→conductive matrix→skin→second conductive film. Permeable ions in the conductive matrix between the first conductive film and skin two-dimensionally receive electric repulsion force by the electrons flowing from the negative pole to the positive pole, and permeate through the skin from the conductive matrix. Electrons permeating through the skin together with the permeating ions induce a reduction reaction.

In the second conductive film from which electrons are moved away, excessive holes are self-biased by the internal electric field of the Schottky barrier formed at the skin-contact area and permeate into the skin to induce the oxidation reaction. The Schottky barrier also prevents electrons from entering into the second conductive film from the skin through the skin-contact surface so that a stable electromotive force of the chemical cell can be maintained.

The second conductive film is electrically separated from the conductive matrix by the insulating film. Therefore, it does not discharge by itself and is not consumed before it is put in contact with skin.

DETAILED DESCRIPTION OF THE PREFERRED EMBODIMENTS

The first embodiment of the invention will be described.

Figure 1A:
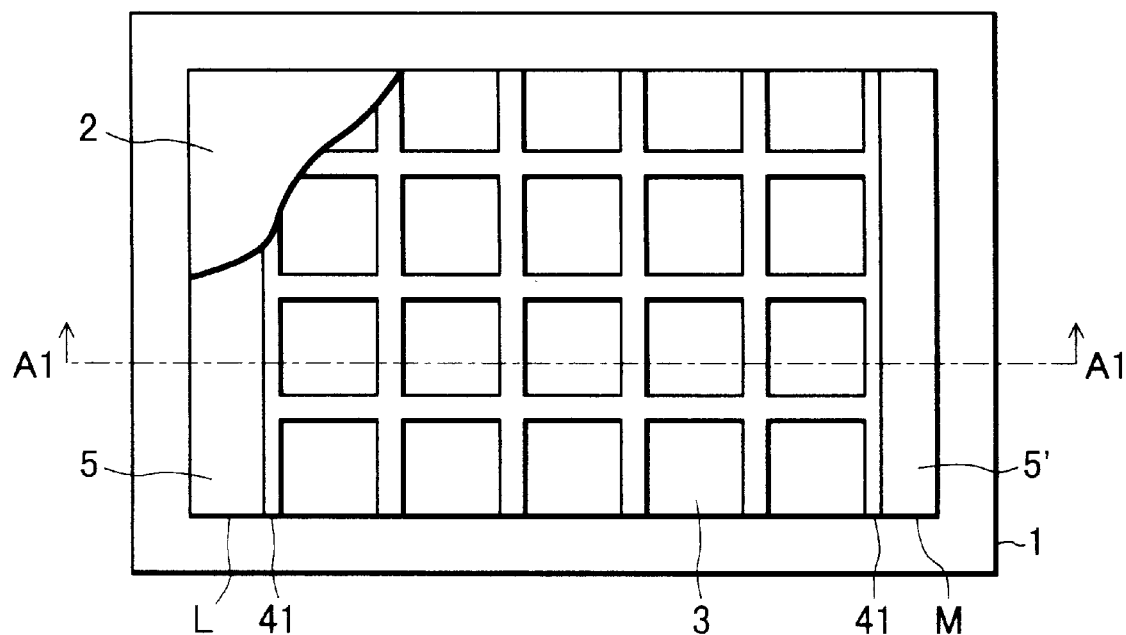
FIG. 1A is a partially broken plan view showing a sheet type transcutaneous dosing element according to a first embodiment of the invention.
Figure 1B:
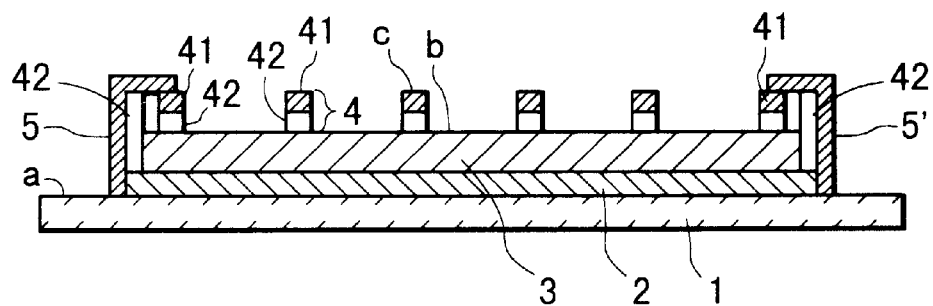
FIG. 1B is a cross sectional view of the element taken along one-dot chain line A1—A1 of FIG. 1A.

FIG. 1A is a partially broken plan view showing a transcutaneous dosing element according to the first embodiment of the invention, and FIG. 1B is a cross sectional view of the element taken along one-dot chain line A1—A1 of FIG. 1A. The transcutaneous dosing element of the first embodiment comprises a plaster 1 as adhesive means, a metal sheet electrode 2 forming the positive pole of a cell, a conductive matrix 3 dispersed with ionic drug to be permeated, a lattice negative electrode containing the negative pole of the cell, and conductive sheets 5, 5' short-circuiting the positive and negative electrodes. The positive pole forming metal electrode 2 is adhered to the adhesive surface of the plaster 1 excepting the peripheral area of the surface. The conductive matrix 3 is mounted on the upper surface of the positive pole forming metal electrode 2, and is conductive gel material dispersed with ionic drug. The negative electrode 4 has a lower non-conductive pad layer 42 in contact with the conductive matrix 3 and the upper semiconductor layer 41. The height of the negative electrode 4 is actually small although it is drawn in FIG. 1B as having a unnegligible height. The positive pole forming sheet electrode 2 may be a metal film completely filled with the same kind of metal, a meshed metal film with regular meshed gaps, or a metal film with perforated patterns. The lattice negative electrode has a two-layer structure and its lattice structure has bars of regular width and space intersected orthogonally or obliquely.

As shown in FIG. 1B, the conductive sheets 5, 5' electrically interconnect the positive pole forming metal electrode 2 and the semiconductor layer 41 at opposite ends L and M of the metal electrode 2. The non-conductive pad 42 electrically separates the conductive sheets 5, 5' and the conductive matrix 3. In place of the conductive sheets 5, 5' a bonding wire may be used.

This transcutaneous dosing element is used by bringing in contact with skin a peripheral area a of the adhesive surface of the plaster 1, an exposed surface b of the conductive matrix 3, and an exposed surface c of the semiconductor layer 41. As the dosing element is adhered to skin to make the conductive matrix 3 and the semiconductor layer 41 simultaneously in contact with the skin, a chemical cell of an external short circuit type is formed at the skin-contact area, by the metal positive electrode 2, negative electrode 4, and electrolyte. The current path is a closed circuit of the semiconductor layer 41→conductive sheets 5, 5',→metal positive electrode 2, conductive matrix 3→skin→semiconductor layer 41.

The conductive sheets 5, 5' electrically short an external circuit of the chemical cell when the dosing element is put in contact with skin. Before being put in contact with skin, the chemical cell is not consumed because the closed circuit of the positive and negative electrodes is not formed.

The metal positive electrode 2 is in surface contact with the conductive matrix 3. As ionic drug salt contained in the conductive matrix 3 is dissociated and permeated through the living body in the form of ions $M^-$, ph of the conductive matrix 3 changes or alkali ions of drug salt is precipitated as metal. Therefore, metal resistant to corrosion, such as a noble metal, is preferably used as the material of the metal positive electrode 2 in order to be durable for long term use. Since an inexpensive material is desired for a disposable type, it is more preferable to use an inexpensive copper containing metal by putting the metal positive electrode 2 in contact with the conductive matrix 3 just before use.

The conductive matrix 3 is made of conductive gel of high polymer, for example, gel of polyvinyl pyrrolidone. In order to avoid problems such as boils of skin produced by a ph change of the matrix during long term use, a ph change may be preferably alleviated by a known measure of mixing material causing neutralization, such as use of a reaction of generating insoluble salt by mixing acid base material such as uric acid and use of ester by mixing alcohol.

The semiconductor layer 41 constituting the negative electrode 4 is generally made of anoxia type oxide semiconductor. The resistivity of semiconductor can be reduced to 1 Ω·cm or lower through film thinning and improvement of the anoxia rate. An n-type low resistance semiconductor thin film can therefore be formed. Such anoxia type oxide semiconductor includes zinc oxide (ZnO), aluminum oxide ($Al_2O_{3-x}$), tin oxide (SnO), lead oxide (PbO), bismuth oxide ($Bi_2O_3$), antimony oxide ($Sb_2O_3$), iron oxide ($Fe_3O_{4-x}$), chromium oxide ($CrO_{2-x}$), molybdenum oxide ($MoO_{2-x}$), niobium oxide ($NbO_{2-x}$), titanium oxide ($Ti_2O_{3-x}$), and the like, all of which are a kind of non-stoichiometric compound.

Such an n-type oxide semiconductor thin film can be formed on an underlying layer by known thin film formation methods such as sputtering, evaporation, and chemical vapor deposition (CVD). Using a polyimide or polytetrafluoroethylene (PTFE) containing resin as an underlying layer, the negative electrode 4 can be formed by one process. Namely, the semiconductor layer 41 is made of n-type oxide semiconductor, and the non-conductive pad 42 is made of underlying resin film.

The n-type semiconductor oxide may be formed on a metal film which is made of a metal element composing a positive ion of the oxide semiconductor. For example, zinc oxide is formed on a zinc film, or aluminum oxide is formed on an aluminum film. In this case, the n-type oxide semiconductor can be formed on the metal film either by the thin film formation method described above or through oxidation of metal surface by acid process or the like. If the semiconductor layer 41 of the two-layer structure of oxide and metal film is used, the lower layer non-conductive pad 42 of the negative electrode 4 is made of a flexible sheet of woolen textile or high polymer and attached to the metal film of the semiconductor layer 41. With this structure, the conductivity of the semiconductor layer 41 increases and the electric loss can be advantageously reduced. The metal is gradually oxidized by water contents at the skin-contact area to form the oxide semiconductor having a stable thickness.

The semiconductor layer 41 constituting the negative electrode 4 may be made of n-type germanium, its alloy, n-type silicon, its alloy, rare earth compound, its mixture, or the like, all of which cause physiological activation by inducing interferon or the like when entered living body. In oxide semiconductors, even if electrons flow into the metal positive electrode when the dosing element is made in contact with skin, an oxidation reaction has priority at a skin-contact surface. Therefore, there is only a small possibility that ionized semiconductor atoms permeate through living body. Inversely, consider the case wherein non-oxide semiconductor of a covalent bond type which is relatively stable against oxidation is used. In this case, as electrons flow into the metal positive electrode when the dosing element is made in contact with skin, holes flow toward the skin-contact surface, charge it positive and make it unstable. Therefore, atoms forming the semiconductor are removed from crystals by an internal electric field due by the Schottky barrier, and become free positive ions which are permeated through a living body. The semiconductor layer 41 made of germanium or the like can therefore be expected to induce cytokinin in a living body.

The conductive sheets 5, 5' shown in FIGS. 1A and 1B may be made of metal foil. Aluminum foil, tin foil, or the like available in markets may also be used.

Sheet type transcutaneous dosing elements shown in FIGS. 1A and 1B were prepared and attached to rats by using the plaster 1. In each dosing element, pure copper was used for the metal positive electrode 2, the width and height of the lattice type negative electrode 4 were set to both 2 mm, the distance between lattice bars (exposed width of the conductive matrix 3) was set to 12 mm, and the conductive matrix 3 was made of gelatin gel dispersed with 0.5 mol sodium citrate and had a thickness of about 2 mm. Three SD male rats constituted one group and the conductive matrix 3 and the negative electrode 4 were made in contact with the hair-cut back of each rat. Concentrations in blood of each rat were measured after 2, 4, 6, and 8 hours. Dummy transcutaneous dosing elements having the same area as above were prepared and attached to a group of rats to compare the concentrations in blood. Each dummy transcutaneous dosing element had only the plaster 1 on which gelatin matrix dispersed with 0.5 mol sodium citrate was coated.

Figure 2:
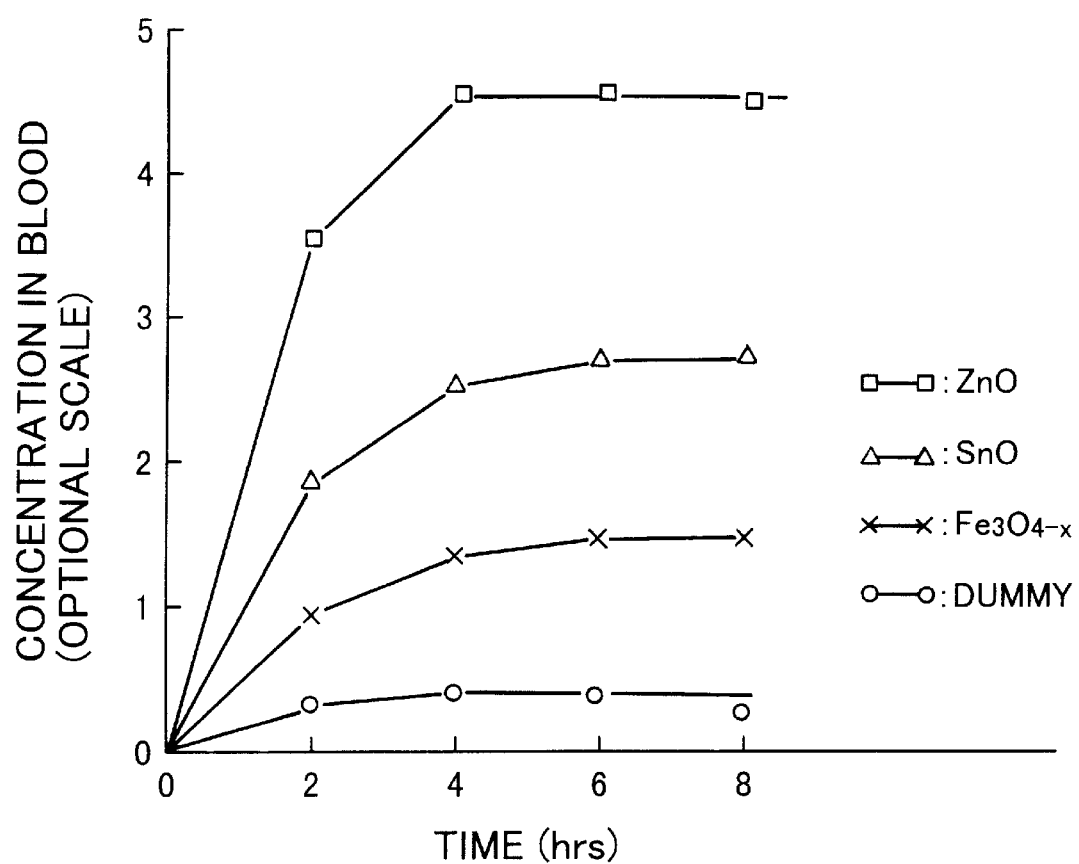
FIG. 2 is a graph illustrating the iontophoresis effects of the element shown in FIGS. 1A and 1B.

FIG. 2 is a graph showing a change of citrate concentration in blood obtained by using different semiconductor layers 41 of the negative electrode 4, in comparison with that of the dummy elements. A concentration in blood higher than the dummy element was observed for all types of the semiconductor layers 41. As compared to simple concentration diffusion, iontophoresis of this embodiment was effective in drug permeation several to ten times. With this iontophoresis, the concentration in blood became constant in 4 hours after the dosing element was attached. As compared with the concentration in blood after 6 hours obtained by using the dummy element, although not shown in FIG. 2, the concentration for the negative electrode of aluminum oxide was about ten times, and that of germanium was about four times.

The iontophoresis effects were also compared between the semiconductor layers 41 of a single layer structure and a two-layer structure of an oxide semiconductor film and a metal film. Iontophoresis transcutaneous dosing elements of these two types were prepared in the following manner. ZnO was deposited to a thickness of 0.5 $\mu$m on a PTFE polymer film, and ZnO was deposited to a thickness of 0.1 $\mu$m on a zinc film. An insulating film of 1 mm thick was adhered to each underlying film, and thereafter they were shaped into the lattice form shown in FIG. 1A. These negative electrodes 4 were mounted on the surface of a gelatin gel layer dispersed with 0.5 mol sodium citrate. The sizes of the metal positive electrode and the lattice type negative electrode were the same as described above. These dosing elements were attached to depilated SD male rats to measure the iontophoresis effects. There was no significant difference between the two types. However, the two-layer structure of an oxide semiconductor layer and a metal layer showed a tendency that the concentration in blood became maximum after 4 hours and it lowered thereafter.

Next, the second embodiment of the invention will be described.

Figure 3:
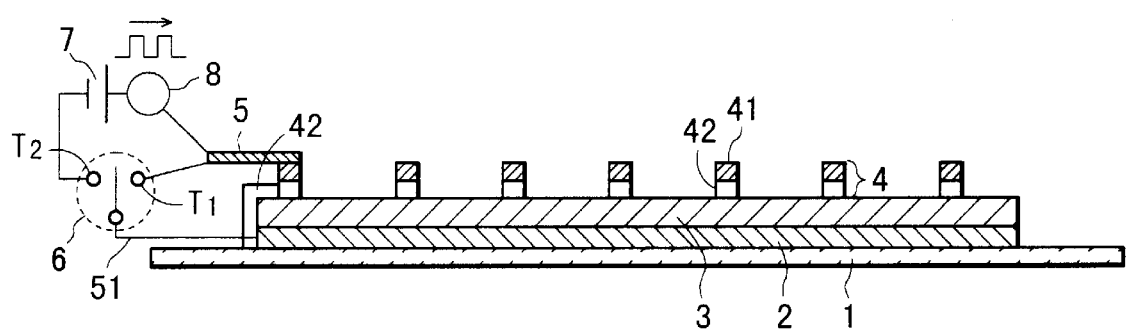
FIG. 3 is a cross sectional view of a sheet type transcutaneous dosing element according to a second embodiment of the invention.

FIG. 3 is a cross sectional view of a transcutaneous dosing element of the second embodiment. A gold thin film sheet serving as a metal positive electrode 2 is adhered to a plaster 1, and a conductive matrix layer 3 is formed on the electrode 2. In forming the conductive matrix layer 3, polyvinyl pyrrolidone gel dispersed with 0.8 mol $\alpha$-tocopherol derivative salt is coated on the electrode 2. Next, a lattice type negative electrode 4 having a width of 2 mm, a height of 1.5 mm, and a lattice bar space of 10 mm is disposed on the conductive matrix 3 in tight contact therewith. The negative electrode 4 has upper and lower layers. The upper layer is a semiconductor layer 41 made of n-type ZnO/Zn of 0.6 mm thick, and the lower layer is a nylon sheet of 0.9 mm thick. The conductive matrix layer 3 of this sheet type transcutaneous dosing element has a size of 40×40 $mm^2$. A conductive wire 51 connected to one end of the metal positive electrode 2 near one side of the dosing element is electrically connected to a movable contact of a switch 6. A conductive film 5 connected to the semiconductor layer 41 of the lattice type negative electrode 4 is connected to one (T1) of fixed contacts of the switch 6. The conductive sheet 5 is also connected to one end of a pulse circuit, the other end of which is connected to the other fixed contact T2 of the switch 6. The pulse circuit to cause tetanus is made of a low voltage (10 V or lower), low frequency pulse oscillator 8 oscillating in the frequency range of 50 to 500 Hz and an oscillator power source 7 serially connected thereto. Tetanic stimulation (or tetanus) are voltage stimuli repetitively applied to synapses.

The pulse polarity of the pulse oscillator 8 is positive on the side of the negative electrode 4 relative to the metal positive electrode 2. The switch 6 and the tetanus circuit are detachable and can be used with different sheet type transcutaneous dosing elements. With the transcutaneous dosing element in contact with skin, a small voltage pulse from the low frequency pulse oscillator 8 increases synaptic plasticity of peripheral nervous systems which are located in a true skin (1–2 mm depth under a skin surface) and physiologically activates skin cells near the pulse applied area. This activation continues for several hours or longer after pulse application (after tetanus), and is called long term potentiation effects (LTP effects). Tetanus by low frequency pulses are used for increasing a drug absorption efficacy through physiological activation of skin surfaces of living body. After the transcutaneous dosing element is put in contact with skin, the movable contact of the switch 6 is turned to the fixed contact T2 side to physiologically activate skin cells, and thereafter, it is turned to the fixed contact T1 side to continue iontophoresis. As described earlier, the LTP effects continue for several hours and thereafter gradually lower. Therefore, for long term iontophoresis, it is preferable to apply tetanus at a frequency of once per several hours. Preferably, the time of tetanus is about one minute for the first time, and about 30 seconds for succeeding times. The pulse frequency and peak voltage are selected depending upon the depth of an affected part and an activated level of peripheral nerves of living body skin. Generally, the deeper the affected area is located, the lower the frequency is set and the higher the peak voltage is set.

Tetanus provide the accumulation effects by repetitive voltage pluses. Therefore, if the voltage pulse has a frequency which presynapic peripheral nerves can discriminate when the pulse is applied thereto, then the LTP effects can be induced. According to experiments of directly applying pulses to nerve fibers, the LTP effects were obtained in the frequency range of 10 Hz to several kHz. However, if pulses are applied transcutaneously, pulses are diverged during transmission in living body so that the frequency range limit becomes more severe. According to the transcutaneous tests, the frequency range from 50 to 500 Hz provided good results. The peak value of a voltage pulse is sufficient if it has about 10 mV or higher at the areas of presynaptic nerve fibers. Preferably it is 0.1 V or higher at the skin-contact area, when the invivo attenuation, frequency, noise level, and the like are taken into consideration.

The iontophoresis effects were checked by attaching the transcutaneous dosing elements shown in FIG. 3 to the haircut and depilated backs of white rabbits. The frequency of the low frequency pulse oscillator 8 was set to 200 Hz and the peak voltage was set to 3 V. Each group was constituted of two white rabbits, and the transcutaneous dosing elements of the same specification were attached to the same area of the rabbit backs to measure the average concentrations of α-tocopherol in blood every second hour. The movable contact of the switch 6 was turned to the fixed contact T1 side for one group, i.e., only the iontophoresis was performed. For the other group, the movable contact of the switch 6 was turned to the fixed contact T2 side to apply tetanus for one minute, and then the movable contact was turned to the fixed contact T1 side. At an interval of five hours, the tetanus was applied for one minute by turning the movable contact to the fixed contact T2 side.

Figure 4:
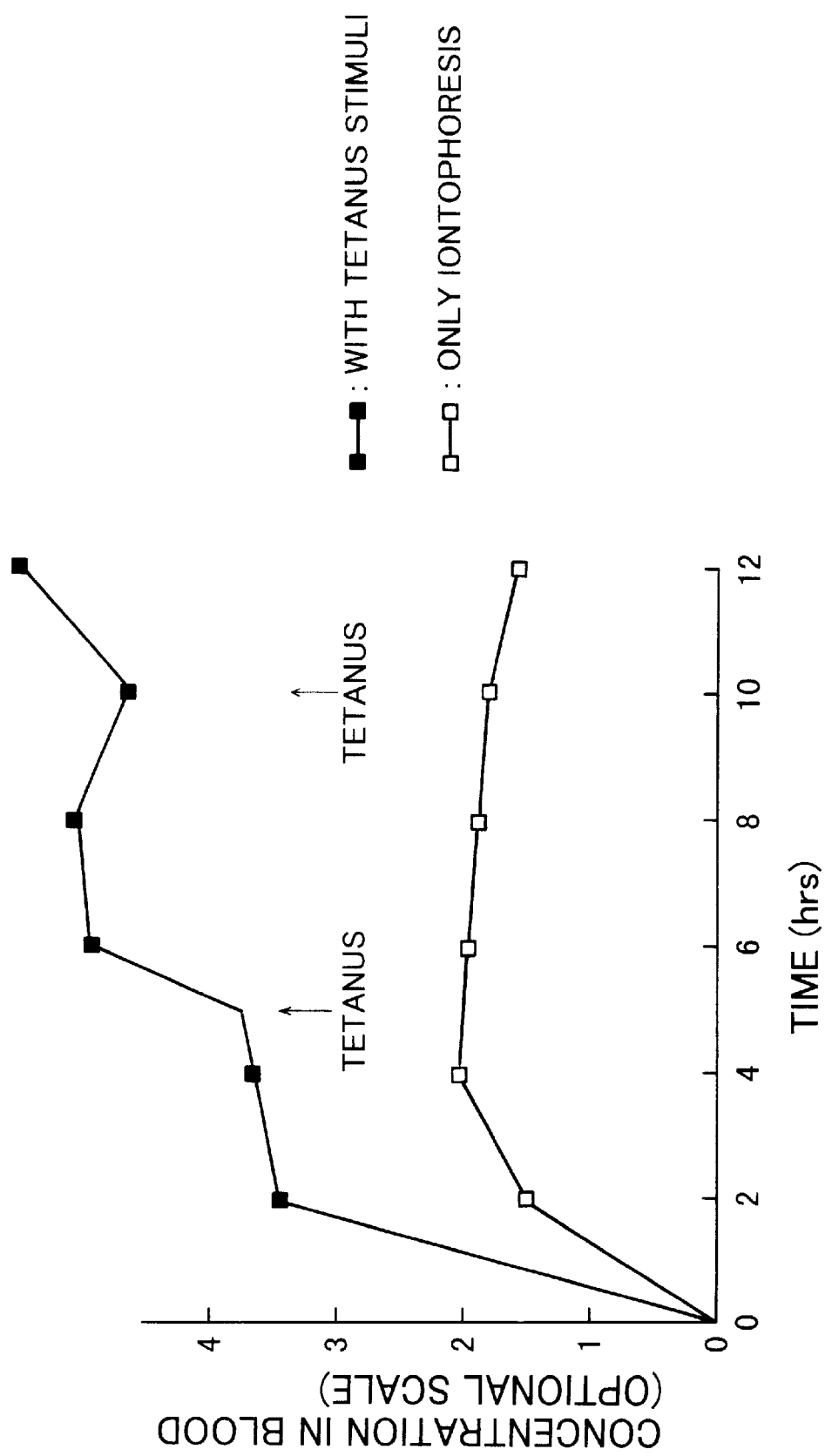
FIG. 4 is a graph illustrating the iontophoresis effects of the element shown in FIG. 3.

The measured results are shown in FIG. 4. As compared to only the iontophoresis, the drug permeation efficiency was increased by two to threefold by introducing tetanus which physiologically activates skin cells. Since the tetanus has the accumulation (memory) effects, the drug permeation efficiency is expected to be further improved by optimizing the magnitude and application frequency of stimuli.

The tetanus effects of the sheet type transcutaneous dosing element shown in FIG. 3 were evaluated in more detail by changing the pulse frequency and peak voltage. In this embodiment, 0.3 mol sodium ascorbate was dispersed in the conductive matrix 3 as ionic drug. A meshed silver layer was used as the metal positive electrode 2, and n-type $Ge_{0.7}Si_{0.3}$ of 1.5 μm thick deposited on an Al thin film was used as the semiconductor layer 41 of the negative electrode 4. The size of the conductive matrix 3 was set to 20×40 $mm^2$. The other materials and dimensions were the same as those used for the measurements shown in FIG. 4.

These transcutaneous dosing elements were attached to the backs of hair-cut SD male rats. Each group was constituted of two rats, and the average concentrations of ascorbic acid in blood were measured every other hour for each group. The measured results are shown in FIG. 5.

Figure 5:
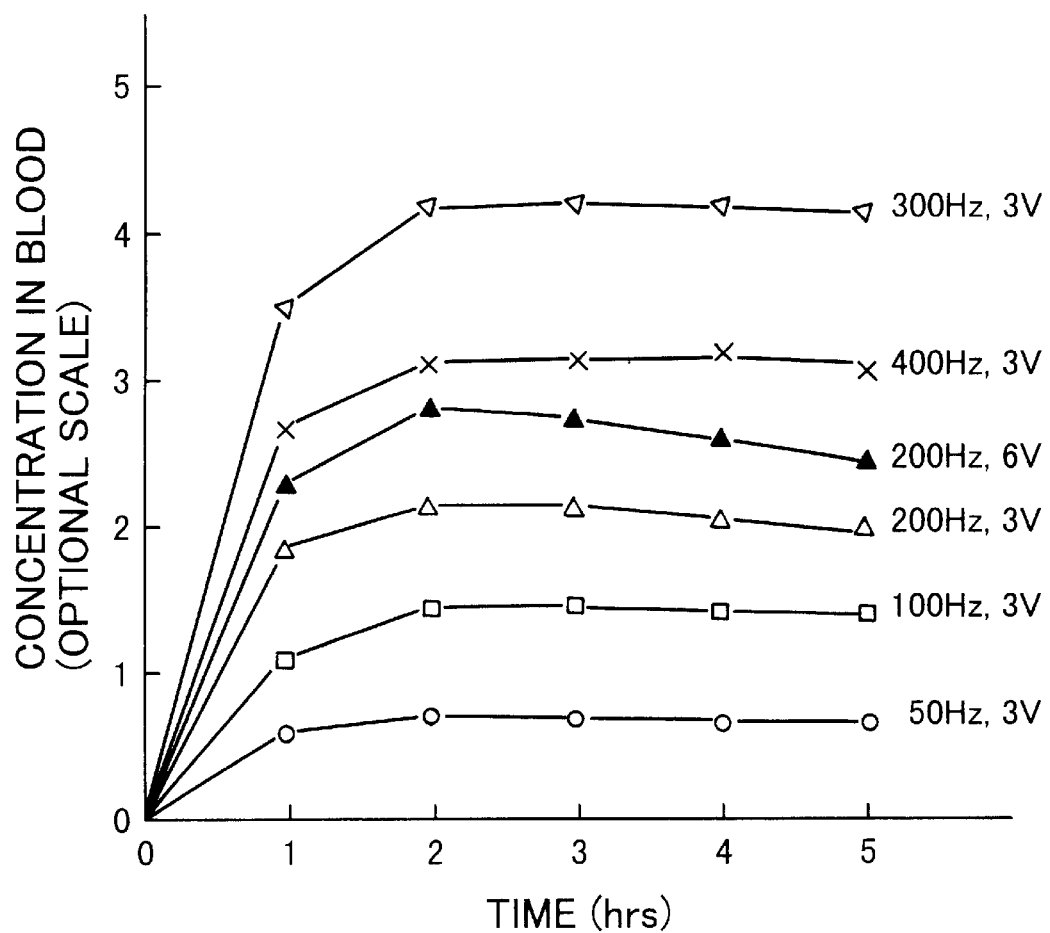
FIG. 5 is a graph illustrating the tetanus stimulus effects of the element shown in FIG. 3.

The data shown in FIG. 5 was measured under the conditions that immediately after the transcutaneous dosing element was attached, low frequency pulses of 3 or 6 V peak voltage were applied and then pulses were stopped to perform iontophoresis. As seen from FIG. 5, the tetanus effects were largest at 300 Hz, however an optimum peak voltage paired with this frequency is unknown. The pulse duty ratio was set to 50%. The tetanus effects were rather large at 6 V than at 3 V at the frequency of 200 Hz. The reduction of the tetanus effects was slightly larger at 6 V than at 3 V. Although not shown, measurements were conducted also at 25 Hz. There was no significant difference from the measurements without tetanus.

From the above observations, it can be presumed that the frequency of tetanus is preferably 50 Hz or higher. Although the peak voltage used in the measurements shown in FIG. 5 was set to 3 and 6 V, the tetanus of 0.1 V at 200 Hz also showed some effects. It is therefore preferable that the peak voltage is from about 0.1 V to 10 V. The frequency of tetanus is preferably 500 Hz or lower.

In the blood test of rats, ascorbic acid as well as germanium and silicon was detected at any frequency and voltage of pulses. In the experiments shown in FIGS. 2 and 4, the concentration in blood of positive ions (metal ions) constituting the semiconductor of the negative electrode 4 was not so high to the degree that it showed a significant difference. Therefore, the experiment results of this embodiment suggest a phenomenon specific to non-oxide semiconductor having a strong covalent bond.

The iontophoresis effects were also observed even if bismuth oxide, lead oxide, antimony oxide, titanium oxide, or the like was used as the material of the semiconductor layer of the negative electrode 4. In addition to the drug used in the above embodiments, the drug dispersed in the conductive pad may be any one or more of an antibiotic drug, anti-epilepsy drug, anti-arrhythmia drug, hormone drug, insulin drug, or the like.

According to the first and second embodiments, a sheet type disposable transcutaneous dosing element can be formed without using an external power source. It is possible to continue to dose drugs in normal daily life, safely, economically, and efficiently, without being anxious about excessive current trouble (such as skin damage) which might to be caused by a skin resistance change when using a portable external power source.

By introducing tetanus which improves the synaptic plasticity of nerves, physiological activation of skin can be induced and the drug permeation efficiency can be improved by iontophoresis. The application field of transcutaneous dosing can thus be expected to be broadened more than before.

Next, the third embodiment of the invention will be described.

Figure 6A:
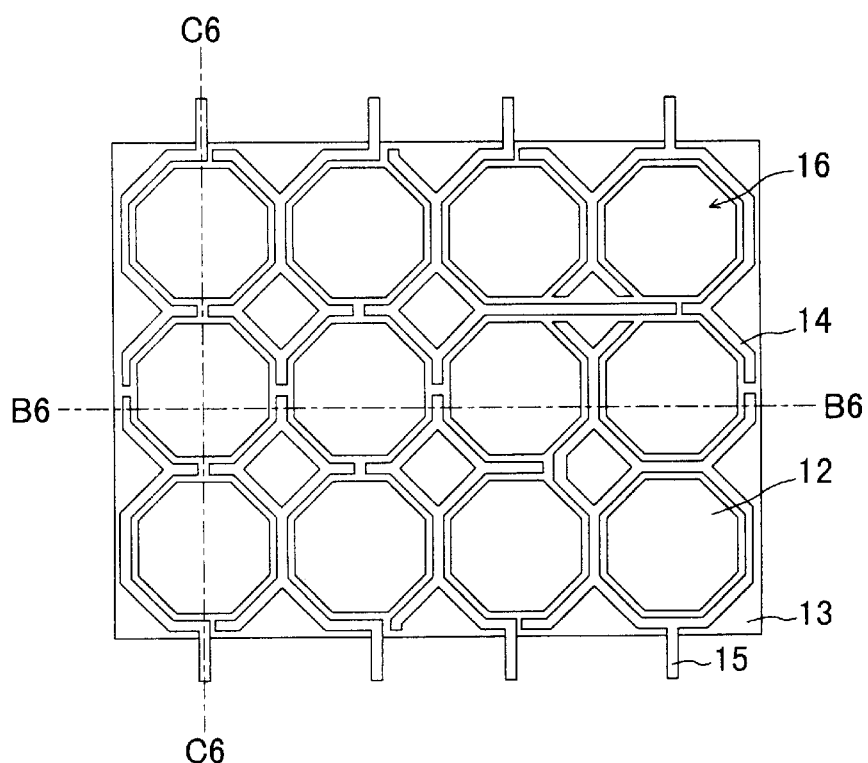
FIG. 6A is a plan view of a lamination type transcutaneous dosing element according to a third embodiment of the invention.
Figure 6B:
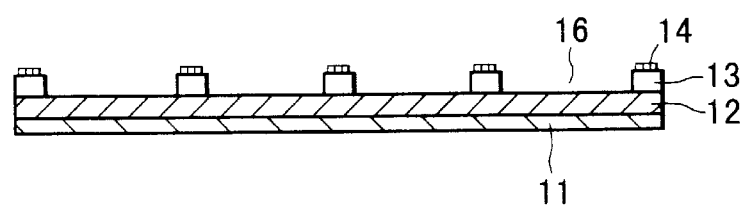
FIGS. 6B and 6C are cross sectional views of the element taken along one-dot chain lines B6—B6 and C6—C6 of FIG. 6A.
Figure 6C:
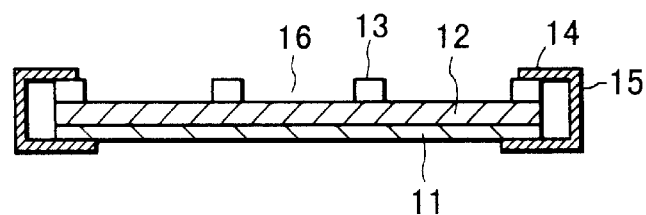

FIG. 6A is a plan view of a lamination type transcutaneous dosing element according to the third embodiment of the invention, FIG. 6B is a cross sectional view taken along one-dot chain line B6—B6 of FIG. 6A, and FIG. 6C is a cross sectional view taken along one-dot chain line C6—C6 of FIG. 6A. The transcutaneous dosing element of the third embodiment is constituted of an active electrode plate 11, a drug layer 12, an insulating plate 13, a counter electrode plate 14, and conductive wires 15. On the surface of the active electrode plate 11, the drug layer 12 is disposed. The insulating plate 13 is disposed on the surface of the drug layer 12, and the counter electrode plate 14 is disposed on the insulating plate 13. The active electrode plate 11, drug layer 12, insulating plate 13, counter electrode plate 14, and conductive wires 15 correspond to the metal positive electrode 2, conductive matrix 3, non-conductive pad 42, semiconductor layer 41, and conductive sheets 5, 5', respectively shown in FIG. 1B. The conductive wire 15 forms a short circuit of the active electrode plate 11 and the counter electrode plate 14 at the area other than the skin-contact area. Similar to the case of FIG. 3, a pulse oscillator, a power source, and a switch may be connected between the active electrode plate 11 and the counter electrode plate 14 to apply tetanus.

With the structure shown in FIGS. 6A to 6C, if the ionic drug dispersed in the drug layer 12 is positively charged, the drug-contact surface of the active electrode plate 11 is made of semiconductor (preferably n-type semiconductor) having a standard single electrode potential lower than the conductive member forming at least the skin-contact surface of the counter electrode plate 14. On the other hand, if the ionic drug is negatively charged, the drug-contact surface of the active electrode plate 11 is made of conductive member (mainly metal) having a standard single electrode potential higher than the counter electrode plate 14. In this case, the skin-contact surface of the counter electrode plate 14 may be one of semiconductor and metal.

Therefore, a stable chemical cell can be formed and iontophoresis is possible without using an external power source. For a disposable transcutaneous dosing element for a short term use purpose, it is sufficient if one of the active electrode plate 11 and the counter electrode plate 14 is made of conductive member having a higher standard single electrode potential than the other (both the electrode plates may be made of metal).

The insulating plate 13 is used for spatially separating the drug layer 12 and the counter electrode plate 14, and made of flexible and water-proof material. In many cases, the conductive wire 15 is made of the same material as the counter electrode plate 14 because of its workability. In many cases, both the active electrode plate 11 and the counter electrode plate 14 are made of a flexible metal foil or meshed metal layer on which conductive member is deposited through plating or evaporation. As shown in FIG. 6A, the counter electrode plate 14 has a constant width disposed along an opening 16. The counter electrode plate 14 is not continuous but is cut on the insulating plate 13 at various positions to be divided into eight portions. Most of the angles between two consecutive sides of the octagon-patterned counter electrode plate 14 are about 120 degrees.

As the transcutaneous dosing element shown in FIGS. 6A to 6C is pressed against the skin of a living body by using a plaster or the like, with the counter electrode plate 14 side being directed to the skin, the drug layer 12 exposed from the opening 16 and the counter electrode plate 14 become in contact with the skin. The counter electrode plate 14 and the drug layer 12 are not connected directly, because of the thickness of the insulating plate 13. An electrically closed circuit is therefore formed from the active electrode plate 11→drug layer 12→skin→counter electrode plate 14→conductive wire 15→active electrode plate 11. An electromotive force is generated by the chemical cell reaction caused by a standard single electrode potential difference between the active electrode plate 11 and the counter electrode plate 14. Ionic drug is therefore permeated into the skin by electric repulsion force to induce iontophoresis. The skin-contact resistances distribute in a large area as the skin-contact area of the transcutaneous dosing element becomes large, depending upon a difference of skin physiological activation between local skin areas and a difference of contact states of the skin and counter electrode plate 14 at local skin areas. The counter electrode pattern into a plurality of portions as shown in FIGS. 6A to 6C can prevent local iontophoresis to be caused by current concentration upon the smallest skin-contact area. Therefore, this electrode pattern is effective for the improvement of drug permeation speed and reproductivity and for the prevention of skin damages by current concentration.

As shown in FIG. 6A, the conductive wires 15 connect each of the eight divided portions of the counter electrode plate 14 to the active electrode plate 11, in an electrically separated state. A closed circuit current generated at each counter electrode plate part having a different skin-contact resistance has a specific current value and flows to the active electrode plate 11. Currents are collected at this active electrode plate 11 and reallocated to the same electromotive force. If the conductive wires 15 are not separately connected to the active electrode plate 11 but they are connected together and then connected in unison to the active electrode plate 11, then this state becomes similar to the case wherein the counter active electrode plate 14 is not divided. Therefore, current concentrates upon the local area having the smallest skin-contact resistance of the drug layer 12 and the counter electrode plate 14. In view of this, the counter electrode plate 14 is connected to the active electrode plate 11 by a plurality of separated conductive wires (preferable by the same number of wires as the number of divided portions of the counter electrode plate). As stated earlier, at least the surface layer of the conductive wire 15 is made of the same material as the material of the skin-contact surface of the counter electrode plate 14. Therefore, if the surface layer of the conductive wire 15 is connected directly to the active electrode plate 11, the chemical cell potential can be maximized so that a large drug permeation force can be induced.

Suitable conductive materials of at least the skin-contact surface or drug-contact surface of the active electrode plate 11 or counter electrode plate 14 are: those having a relatively large standard single electrode potential, including noble metal such as gold, silver, platinum, palladium, and iridium, and metal such as copper; and those having a relatively small standard single electrode potential, including oxide semiconductor such as zinc oxide, tin oxide, aluminum oxide, titanium oxide, indium oxide, and bismuth oxide, non-oxide semiconductor such as germanium, silicon/germanium solid solution, and boron nitride, some metals such as manganese and iron, and nonmetal conductors such as carbon. These materials are used in combination in accordance with the kind of ionic drug and the use conditions.

There is a tendency that the larger opening ratio of the counter electrode plate 14 which ratio determines a skin-contact area of drug, the more the drug permeation amount per unit area. However, since the acceleration electric field becomes weaker at the position in the opening 16 as the distance of the position from the counter electrode plate 14 becomes longer, the iontophoresis effects lower. In other words, there is a trade-off between the permeation area and the electric field in each opening. Therefore, the opening 16 of the counter electrode plate is generally formed as an aggregation of a plurality of openings. The counter electrode plate 14 separated from the drug layer 12 by the insulating plate 13 is disposed around each opening 16. If the counter electrode plate 14 surrounding each opening 16 is divided into a plurality of portions each electrically separated, ion permeation current flows independently at the low resistance area and at the high resistance area even if the skin-contact resistance (contact resistance and epidermal resistance) greatly changes at local areas. It is therefore effective in increasing the permeation amount of the whole element even if the permeation speed is different at each local area. Electrical interconnection between the divided portions of the counter electrode plate 14 and the active electrode plate 11 is achieved preferably by conductive wires 15 same in number as the number of divided portions, or by a plurality of conductive wires 15 each connected to several divided portions of the counter electrode plate 14. If the conductive wires 15 of all the portions of the counter electrode plate 14 are connected together and then connected to the active electrode plate 11 at one point, although this point is not the skin-contact area, current is likely to concentrate upon the portion of the counter electrode plate 14 having the smallest skin-contact resistance.

Figure 7:
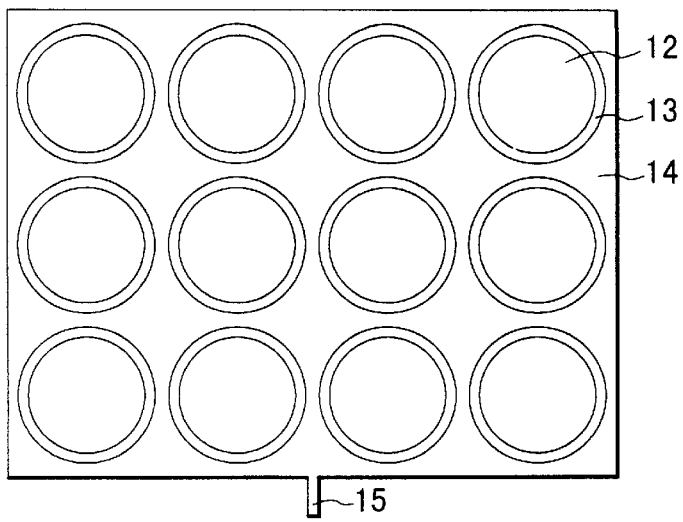
FIG. 7 is a plan view showing the shape of a comparative example of a lamination type transcutaneous dosing element.

In order to evaluate the effects of the transcutaneous dosing elements shown in FIGS. 6A to 6C, transcutaneous dosing elements such as shown in FIG. 7 were prepared.

FIG. 7 is a plan view corresponding to FIG. 6A. This element shown in FIG. 7 has circular openings and the same opening ratio of 60% as that of the element shown in FIGS. 6A to 6C. The counter electrode plate 14 is not divided but integral at the area other than the openings. Therefore, only a single conductive wire 15 is used which corresponds to the conductive wire 15 of FIG. 6C interconnecting the active electrode plate 11 and the counter electrode plate 14. The other structures are the same as those shown in FIGS. 6A to 6C.

In the elements shown in FIGS. 6A to 6C and FIG. 7, the element size was set to 3×4 cm$^2$, a gold plated iron plate of 35 $\mu$m thick was used as the active electrode 11, an iron plate of 35 $\mu$m thick with a zinc oxide film formed on the surface thereof was used as both the counter electrode plate 14 and the conductive wire 15, a polyvinyl pyrrolidone layer of about 1 mm thick with L—sodium asparate was used as the drug layer 12, and a foamed polyethylene plate was used as the insulating plate 13. The elements shown in FIGS. 6A to 6C and FIG. 7 were attached to the hair-cut and shaved backs of SD male rats, two rats constituting one group, and a change of the concentrations of aspartic acid in blood was measured by using time as the parameter. In order to compare with the data without iontophoresis, dummy elements shown in FIG. 7 whose conductive wire 15 is cut to disconnect the current path between the active electrode plate 11 and the counter electrode plate 14 were prepared. The data of each group is shown in FIG. 8.

Figure 8:
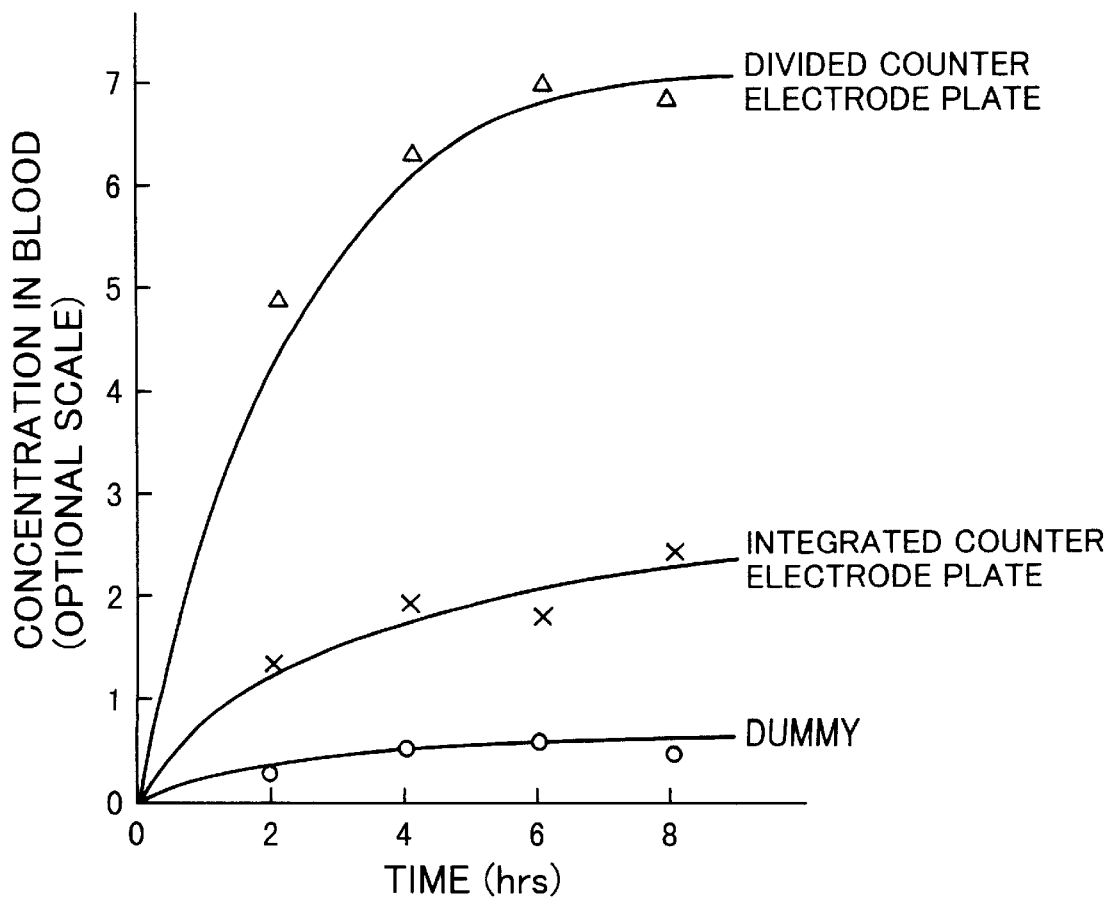
FIG. 8 is a graph showing transcutaneous absorption data of drug using the transcutaneous dosing elements shown in FIGS. 6A to 6C and FIG. 7.

As seen from FIG. 8, a large amount of aspartic acid was transcutaneously absorbed by both the elements shown in FIGS. 6A to 6C and FIG. 7 more than the dummy element (no current conduction), and the iontophoresis effects were observed. It can be seen however that there is a large difference of the iontophoresis effects between the elements shown in FIGS. 6A to 6C and FIG. 7. Namely, the element shown in FIGS. 6A to 6C shows the concentration about ten times that of the dummy element, whereas the element shown in FIG. 7 shows the concentration about three times. The reason of a large difference of the iontophoresis effects, although the drug concentration and the skin-contact area (opening ratio) are the same, may be ascribed to a large local difference of skin-contact resistance as described previously. Specifically, with the element shown in FIG. 7, there is a concentrated current flow in the area having the smallest skin-contact resistance and the drug layer only in the local area operates. With the element shown in FIGS. 6A to 6C, however, each of the eight portions of the counter electrode plate independently operates in accordance with its local skin-contact resistance. It can be therefore presumed that the absorption amount of the whole area can be increased even if there is a difference of a transcutaneous absorption efficiency at each divided area. Remarkable skin damages were rarely observed on the rats skin to which the element shown in FIGS. 6A to 6C was attached for 8 hours, whereas redness and edemata were observed in a local skin area when the element shown in FIG. 7 was used, which suggests a concentrated current flow in this local skin area.

Figure 9A:
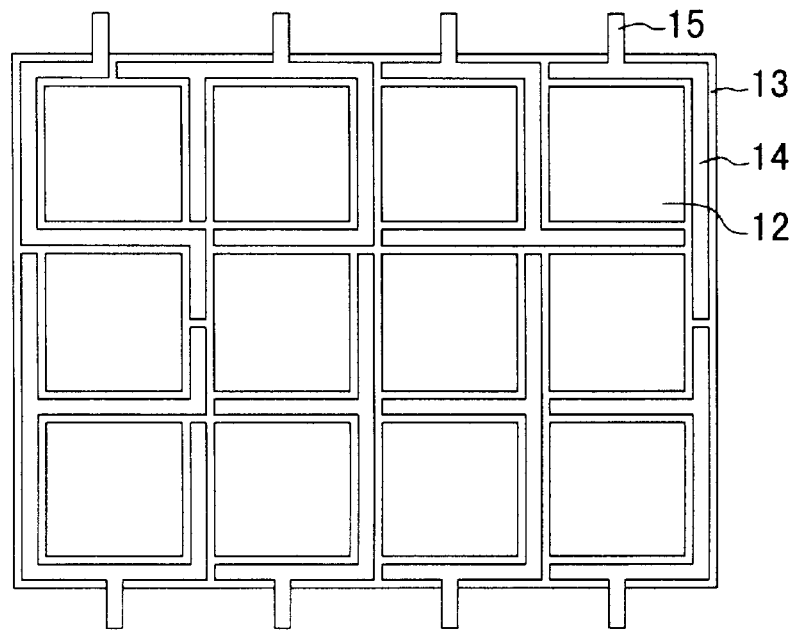
FIGS. 9A and 9B are plan views showing the counter electrode shapes and wires of transcutaneous dosing elements according to modifications of the third embodiment.
Figure 9B:
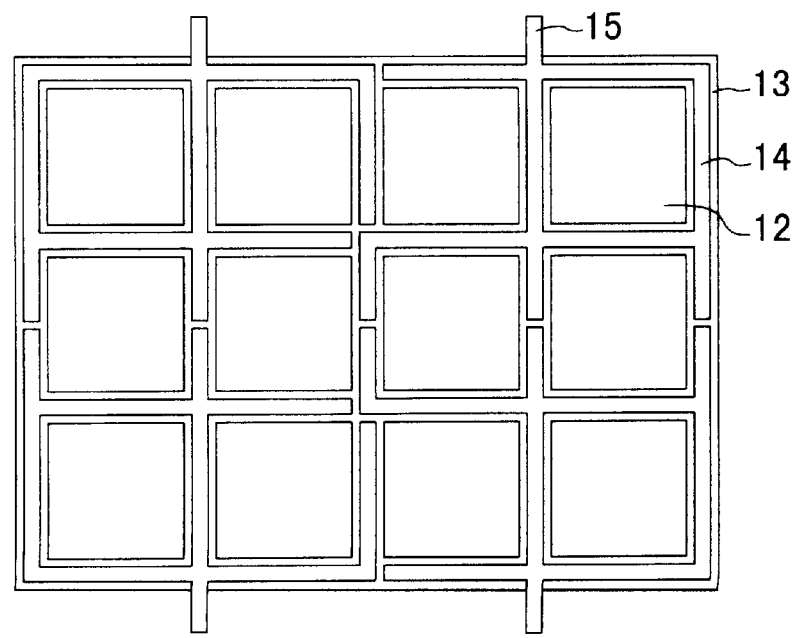

FIGS. 9A and 9B are plan views showing the structures of transcutaneous dosing elements according to modifications of the third embodiment. The element shown in FIG. 9A has eight divided portions of the counter electrode plate 14, and the element shown in FIG. 9B has four divided portions of the counter electrode plate 14. The opening shape of these elements is rectangular and the angle between two consecutive sides of the counter electrode plate 14 is 90 degrees. The counter electrode plate 14 is divided into a plurality of portions on the insulating plate 13 so that the portions are each electrically separated. The other structures are similar to those shown in FIGS. 6A to 6C. As shown in FIG. 6C, the conductive wires 15 of these elements are bent downward perpendicular to the drawing sheet, and again bent inward by 90 degrees to be connected to the bottom surface of the active electrode plates 11. The conductive wire 15 is made of the same material as the counter electrode plate 14.

Figure 10:
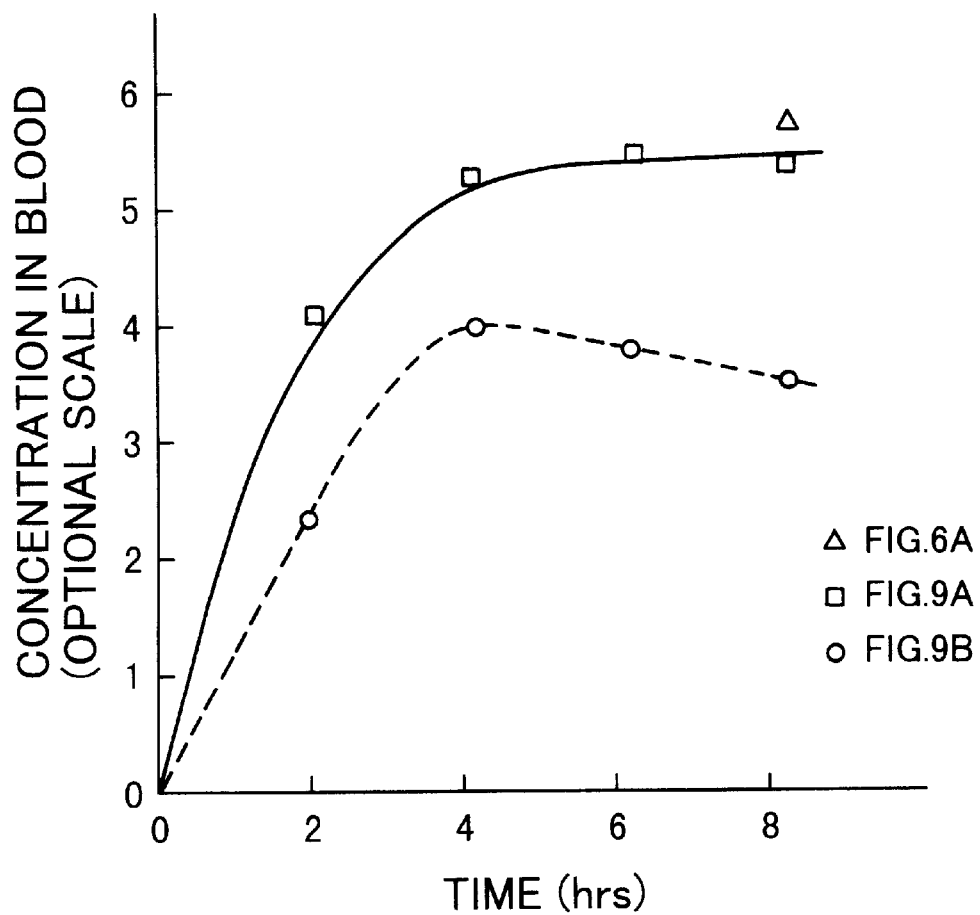
FIG. 10 is a graph showing transcutaneous absorption data of drug using the transcutaneous dosing elements shown in FIGS. 9A and 9B and FIG. 6A.

Transcutaneous dosing elements having the upper surface size of 3×4 cm$^2$ and an opening ratio of 70% were prepared. An iron plate of 35 $\mu$m thick with Au—Ag—Cu alloy deposited on the surfaces thereof using electron beams was used as the active electrode plate 11, matrix of gelatin dispersed with L-ascorbyl-magnesium of about 1 mm thick was used as the drug layer 12, fluorine-contained rubber of about 1 mm thick was used as the insulating plate 13, and an iron plate of 35 $\mu$m plated with tin and then surface oxidized to form an $SnO_2$ film was used as the counter electrode plate 14 and the conductive wires 15. In order to compare the transcutaneous absorption state of drug, the two patterns shown in FIGS. 9A and 9B were prepared. The elements were attached to the hair-cut and depilated backs of white rabbits, two rabbits constituting one group, and the concentrations of ascorbic acid in blood were measured every second hour. The results are shown in FIG. 10. Irrespective of the same concentration of L-ascorbyl-magnesium in the drug layer 12 and the same skin-contact area (opening ratio), the peak concentration in blood for the element shown in FIG. 9B was about 80% of that for the element shown in FIG. 9A. There was a tendency that the concentration in blood gradually lowers as time lapses. After 8 hours, edemata were observed on the rabbit skin near at the corners where the counter electrode plate 14 shaped by 90 degrees.

For comparison, the transcutaneous dosing elements shown in FIGS. 6A to 6C, whose drug layer 12 was replaced by matrix of gelatin dispersed with L-ascorbyl-magnesium, were attached to the hair-cut and depilated backs of white rabbits for 8 hours. After the elements were removed and the skins were checked. Redness and edemata were not observed. The concentrations of ascorbic acid in blood were in the same order as the elements shown in FIG. 9A although the opening rate is as low as 60%.

The above experimental results indicate that the effects of current density rise at the bent portions (corners) of the opening peripheries can be relaxed and skin damages can be suppressed, if the opening shape of the counter electrode plate 14 is a polygon having an angle larger than 90 degrees between two consecutive sides. The results also indicate that the larger the number of divided portions of the counter electrode plate 14 to be separately connected to the active electrode plate 11, the drug permeation (iontophoresis) becomes more difficult to occur only in a local area where current is concentrated, and that the total transcutaneous absorption amount increases. This difficulty provides probable effects of reducing generation of skin damage to be caused by current concentration. Although the opening shape of the counter electrode plate 14 shown in FIG. 6A is a polygon having an apex angle larger than 90 degrees, the opening shape may be a circle such as shown in FIG. 7, and a shape surrounded by smoothly connected curved lines along an outer periphery of a polygon whose apex angles are larger than 90 degrees. These shapes like the polygon having a large apex angle are obviously effective for relaxing the current concentration at sharp corners.

Next, the fourth embodiment will be described.

Figure 11:
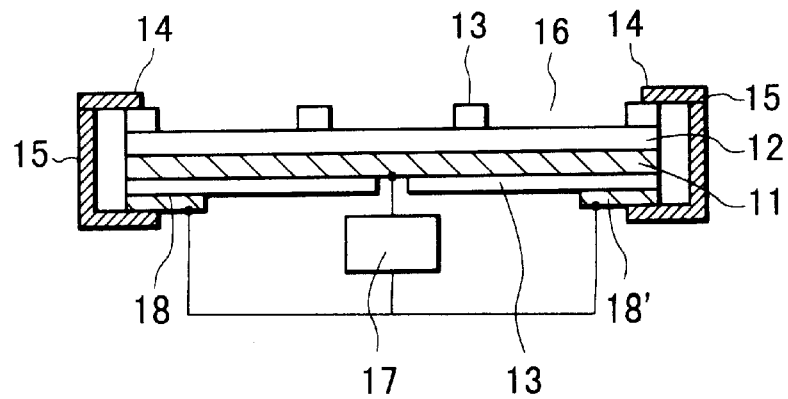
FIG. 11 is a cross sectional view showing the structure of a transcutaneous dosing element according to a fourth embodiment of the invention.

Transcutaneous dosing elements prepared for the fourth embodiment have the same opening pattern as the counter electrode plate 14 shown in FIG. 6A and have an electronic switch capable of breaking skin generation at a predetermined interval. The electronic switch 17 is mounted on the area other than the skin-contact area of the element, i.e., on the back side of the element. FIG. 11 shows this state and corresponds to the cross sectional view taken along one-dot chain line C6—C6 of FIG. 6A. Referring to FIG. 11, a conductive wire 15 connected to each of eight divided portions of the counter electrode plate 14 is connected, on the bottom side of the element (not in contact with skin), to one of two electrode plates 18 and 18' which are disposed on the bottom peripheral areas of a thin insulating film 13 having a through hole and being in tight contact with the bottom of the active electrode plate 11. The surface of the electrode plate 18, 18' is made of the same material as the surface of the active electrode layer 11. In FIG. 11, four conductive wires 15 are connected to the electrode plate 18. The other four conductive wires 15 are connected to the electrode plate 18'. One end of the electronic switch 17 is connected via the through hole to the active electrode plate 11 by a lead wire. The other end of the electronic switch 17 is connected by lead wires to the electrode plates 18 and 18' at points other than the interconnection points of the conductive wires 15. With the above structure, the electronic switch 17 operates each portion of the counter electrode plate 14 to synchronously perform skin current switching, without losing the above-mentioned separate connection effects of each of the plurality of portions of the counter electrode plate 14.

The electronic switch 17 shown in FIG. 11 has a battery power source, a known switching element, and other circuit elements. The electronic switch 17 intermittently stops current of the transcutaneous dosing element at a predetermined interval, the current flowing between the counter electrode plate 14 and the active electrode plate 11. The active electrode plate 11 and the electrode plates 18 and 18' were made of a thin iron plate of 35 μm thick plated with rhodium, the drug layer 12 was made of polyvinyl pyrrolidone gel of about 1 mm thick dispersed with 0.8 mol α-tocopherol derivative salt, the insulating plate 13 was made of foamed polyethylene of 0.4 mm thick, and the counter electrode plate 14 and the conductive wires 15 were made of an iron plate of 35 μm thick plated with manganese. In this case, both the active electrode plate 11 and the counter electrode plate 14 were made of metal. The size of the transcutaneous dosing element is 3×4 cm² like the element shown in FIGS. 6A to 6C.

The concentrations of α-tocopherol in blood were measured after 6 hours from when the transcutaneous dosing elements were attached to the hair-cut and shaved backs of SD male rats, with the turn-off frequency of the electronic switch 17 being set to 250 Hz (duty ratio: 1:1). For comparison, transcutaneous dosing elements similar to the above structure were prepared and attached to another group of SD male rats, with the turn-off frequency of the electronic switch 17 being set to zero, i.e., always with the current conduction. The concentration in blood after 6 hours was larger by 3.5 to 4 times for the embodiment elements than comparison elements, indicating that pulsating current conduction is effective for transcutaneous absorption of electrically neutral drug. In the turn-off frequency range of 50 to 500 Hz, the transcutaneous absorption effects higher than d.c. current conduction were confirmed. This can be ascribed to superposition of the effects of physiological activation of skin by small pulse voltage repetitive stimuli called tetanus of nervous fibers, especially in synapse regions.

The electronic switch inserted into an external circuit between the active electrode plate 11 and the counter electrode plate 14 intermittently cuts the current conduction at a proper frequency in the range of 50 to 500 Hz and changes transcutaneous current into low frequency pulses to induce so-called electroporation phenomenon. Accordingly, electrically neutral drug can be transcutaneously permeated and synaptic plasticity of peripheral nerves distributed in the subcutaneous region can be enhanced. Namely, excitation potentials of post-synaptic nerve fibers are raised and tissues in this area are physiologically activated to induce the synapse LTP effects. Accordingly, the drug transcutaneous absorption efficiency increases to promote iontophoresis.

In the third and fourth embodiments, a chemical cell, a so-called biocell, is formed by skin-contact to induce iontophoresis. These embodiments are not limited to use only the biocell, but a conventional external power source type may be used.

All the active electrode plate 11, counter electrode plate 14, conductive wires 15, and electrode plates 18 and 18' were made of a stainless steel of 35 μm thick to form another type of elements shown in FIG.11. This element therefore does not generate skin current even if the electronic switch of FIG. 11 is used. Instead of this electronic switch, a battery power source for transcutaneous current conduction and a timer were connected. The polarity of the battery was set positive to the active electrode 11, and negative to the counter electrode plate 14. The drug layer 12 was made of a polyvinyl pyrrolidone gel layer dispersed with valethamate bromide of about 1 mol %. The size and shape of the element and other structures were the same as those of the transcutaneous element shown in FIG. 11.

These transcutaneous dosing elements were attached to the hair-cut and depilated backs of white rabbits for 6 hours, the timer was set to a cycle of one hour for current conduction and one hour for breaking current conduction, and the applied voltage between electrodes was set to 3 V. Even under the conditions of the element loading time of 6 hours and the total current conduction time of 3 hours, valethamate ions were detected 5 to 6 times larger than non-current conduction. For comparison, the timer was set to the total current conduction time of 6 hours (continuous current conduction during the element loading time of 6 hours). In this case, the concentration of valethamate ions in blood was higher by about 50% than the current conduction of 3 hours. However, considerable skin damage (including vessicles, redness, hematomata, and etc.) were observed at the skin-contact area of the counter electrode plate 14. In the case of the above-described current conduction of 3 hours in total, only slight skin damage (redness and etc.) was observed. No symptom was indicated as to considerable skin damage especially near corners of a polygon electrode plate. As in this embodiment, there was a tendency that skin damage is more likely to occur during skin current conduction by the external power source than a biocell (internal power source current conduction).

In addition to drugs described in the above embodiments, the transcutaneous dosing element of these embodiments may use various types of an antibiotic drug, anti-epilepsy drug, anti-arrhythmia drug, hormone drug, secretive drug, and the like.

As described so far, the lamination, sheet type disposable transcutaneous dosing element of the third and fourth embodiments can increase the transcutaneous absorption efficiency, improve reproductivity, and reduce skin damage, all at the same time.

The embodiments are applicable not only to the element with a skin-contact chemical cell and without an external power source but also to an element with an external power source. An electronic switch and a timer may be inserted into an external circuit at the area not in contact with skin, the external circuit connecting the active electrode plate and the counter electrode plate, to thereby control the pulse conduction and current conduction time. Any type of plus, minus, and neutral ions of a drug can be selected and the application field can be broadened. Depending upon the type of drug, the materials of the active electrode plate and the counter electrode plate can be selected from a broad range including metal, semiconductor, and nonmetallic conductor. The application field of the transcutaneous dosing element can be broadened further.

The present invention has been described in connection with the preferred embodiments. The invention is not limited only to the above embodiments. It is apparent that various modifications, improvements, combinations, and the like can be made by those skilled in the art.

I claim:

1. A transcutaneous dosing element comprising:

an adhesive sheet member having a skin-contact surface;

a first conductive film disposed on a partial area of the skin-contact surface of said adhesive sheet member;

a conductive matrix adapted to be disposed on said first conductive film, said conductive matrix being dispersed with drug to be permeated through skin;

a second conductive film disposed on said conductive matrix, said second conductive film having a plurality of openings distributed on a surface of said conductive matrix, and said second conductive film having a single standard electrode potential which is different from a single standard electrode potential of the first conductive film;

an insulating film disposed between said conductive matrix and said second conductive film in a manner such that an electric short path is not formed between said conductive matrix and said second conductive film, said insulating film having a plurality of openings distributed on the surface of said conductive matrix; and a connection member for electrically interconnecting said first conductive film and said second conductive film;

wherein when said adhesive sheet member is adhered to skin, an electromotive force generated due to a difference between the standard single electrode potential of the first conductive film and the standard single electrode potential of the second conductive film causes an electric current to flow through an electric circuit that includes each of said first conductive film, said conductive matrix, the skin to which the adhesive sheet member is adhered, said second conductive film, and said connection member.

2. A transcutaneous dosing element according to claim 1, wherein said first conductive film comprises a metal and said second conductive film comprises a semiconductor.

3. A transcutaneous dosing element according to claim 2, wherein said second conductive film comprises an anoxia oxide semiconductor selected from a group consisting of zinc oxide, aluminum oxide, tin oxide, lead oxide, bismuth oxide, antimony oxide, iron oxide, chromium oxide, molybdenum oxide, niobium oxide, and titanium oxide.

4. A transcutaneous dosing element according to claim 1, wherein said second conductive film is divided into a plurality of disconnected portions which are separately connected to said first conductive film by different connection members.

5. A transcutaneous dosing element according to claim 4, wherein said plurality of openings in said insulating film and said second conductive film each have one of: (i) a polygon shape whose each two consecutive sides have an angle therebetween which is larger than 90 degrees, and (ii) a shape surrounded by smoothly connected curved lines along an outer periphery of the Polygon shape.

6. A transcutaneous dosing element according to claim 4, wherein one of said first and second conductive films comprises a semiconductor and the other comprises a metal, and wherein said metal has a standard single electrode potential which is higher than a standard single electrode potential of said semiconductor.

* * * * *